US008155906B2

(12) United States Patent
Andersson et al.

(10) Patent No.: US 8,155,906 B2
(45) Date of Patent: Apr. 10, 2012

(54) METHOD AND SYSTEM FOR CURVE QUALITY CONTROL

(75) Inventors: Karl Andersson, Uppsala (SE); Peter Borg, Uppsala (SE)

(73) Assignee: GE Healthcare Bio-Science AB, Uppsala (SE)

( * ) Notice: Subject to any disclaimer, the term of this patent is extended or adjusted under 35 U.S.C. 154(b) by 314 days.

(21) Appl. No.: 10/400,158

(22) Filed: Mar. 26, 2003

(65) Prior Publication Data
US 2004/0002167 A1    Jan. 1, 2004

Related U.S. Application Data

(60) Provisional application No. 60/367,806, filed on Mar. 27, 2002.

(30) Foreign Application Priority Data

Mar. 27, 2002    (SE) ...................... 0200949

(51) Int. Cl.
*G01R 13/00*    (2006.01)
(52) U.S. Cl. .................. 702/69; 702/71; 702/73; 702/79
(58) Field of Classification Search ............... 205/777.5, 205/775, 787; 706/19–21; 204/412, 406; 435/7.1, 7.4, 975; 436/501, 518, 808; 702/19, 702/190
See application file for complete search history.

(56) References Cited

U.S. PATENT DOCUMENTS

| 5,242,828 | A | | 9/1993 | Bergström et al. ........... 435/291 |
| 5,861,254 | A | * | 1/1999 | Schneider et al. ................ 435/6 |
| 5,955,729 | A | | 9/1999 | Nelson et al. ................. 250/282 |
| 6,019,896 | A | | 2/2000 | Mansfield et al. ........... 210/198.2 |
| 6,243,615 | B1 | * | 6/2001 | Neway et al. ................. 700/108 |
| 6,287,765 | B1 | * | 9/2001 | Cubicciotti ...................... 435/6 |
| 6,289,328 | B2 | * | 9/2001 | Shaffer .......................... 706/20 |
| 6,350,369 | B1 | * | 2/2002 | Lewis et al. ................ 205/777.5 |
| 6,829,540 | B1 | * | 12/2004 | Pidgeon et al. .................. 702/22 |
| 6,950,752 | B1 | * | 9/2005 | Friend et al. .................... 702/19 |

FOREIGN PATENT DOCUMENTS

| DE | 100 05 301 A1 | 8/2001 |
| JP | 2000-180453 | 6/2000 |
| WO | WO 97/09618 | 3/1997 |

OTHER PUBLICATIONS

Sadana et al, A kinetic analysis using fractals of cellular analyte-receptor binding and dissociation, 2001, Biotechnol Appl Biochem, 33, 17-28.*

(Continued)

*Primary Examiner* — N. Yang

(57) ABSTRACT

A method of analysis wherein molecular interactions at one or more sensing surface areas are detected and respective response curves representing the progress of each interaction with time are produced, and wherein a resulting set of response curves is subjected to a quality assessment procedure which comprises representing the response curves with one or more quality descriptors, applying a quality classification method to the descriptors to find outliers, and removing the outliers. The invention also relates to an analytical system including means for classifying the response curves with regard to quality, a computer program for performing the classification, and a computer program product containing the program.

19 Claims, 5 Drawing Sheets

OTHER PUBLICATIONS

Li et al., Model-based analysis of oligonucleotide arrays: expression index computation and outlier detection, Jan 2001 PNAS; 98(1), pp. 31-36.*

Shank-Retzlaff et al., Analyte gradient-surface Plasmon resonance: a one-step method for determining kinetic rates and macromolecular binding affinities, 2000 Anal Chem, 72: pp. 4212-4220.*

Myszka, Improving biosensor analysis, 1999 J Mol Recog, 12: pp. 279-284.*

Myszka, Improving biosensor analysis, 1999, J Mol Recognition, 12: pp. 279-284.*

Ruppert et al., Trimmed least squares estimation in the linear model, 1980, J Am Stat Ass, 75(372):pp. 828-838.*

Borg, P. et al., "Large-Scale Quality Control of Curves Describing Molecular Interactions," in *Proceedings of Bioinformatics 2002*, Bergen, Norway, Apr. 4-7, 2002.

* cited by examiner

METHOD AND SYSTEM FOR CURVE QUALITY CONTROL

CROSS-REFERENCE TO RELATED APPLICATION

This application claims the benefit of U.S. Provisional Patent Application No. 60/367,806 filed Mar. 27, 2002 and Swedish Patent Application No. 0200949-6 filed Mar. 27, 2002, both of which are incorporated herein by reference in their entireties.

BACKGROUND OF THE INVENTION

1. Field of the Invention

The present invention relates to a method of analyzing molecular binding interactions at a sensing surface, and more particularly to the quality control of the resulting data describing the molecular interactions. The invention also relates to an analytical system including such a quality control as well as to a computer program for performing the method, and a computer system and computer program product, respectively, containing the program.

2. Description of the Prior Art

Analytical sensor systems that can monitor interactions between molecules, such as biomolecules, in real time are gaining increasing interest. These systems are often based on optical biosensors and usually referred to as interaction analysis sensors or biospecific interaction analysis sensors. A representative biosensor system is the Biacore® instrumentation sold by Biacore AB (Uppsala, Sweden) which uses surface plasmon resonance (SPR) for detecting interactions between molecules in a sample and molecular structures immobilized on a sensing surface. With the Biacore® systems it is possible to determine in real time without the use of labeling, and often without purification of the substances involved, not only the presence and concentration of a particular molecule in a sample, but also additional interaction parameters such as, for instance, the association rate and dissociation rate constants for the molecular interaction. The Biacore® system is currently used in life science research as well as in the drug discovery industry and in food analysis.

A typical output from the Biacore® and similar biosensor systems is a graph or curve describing the progress of the molecular interaction with time. This curve, which is usually displayed on a computer screen, is often referred to as a "sensorgram". While it is possible for the operator of the biosensor instrument to assess the quality of the produced sensorgrams manually and discard any sensorgram of unacceptable quality, the current trend towards systems with ever increasing throughput and information density in the analyses performed puts a more and more heavy burden on the operator.

Accordingly, there remains a need in this field for improved methods and products for facilitating quality assessment in biosensor systems, especially where large sets of sensorgrams are produced.

BRIEF SUMMARY OF THE INVENTION

It is an object of the present invention to improve the operation of a biosensor system of the type referred to above by providing means for data processing of especially a large set of detection curves to classify the curves with regard to quality. Such quality classification may particularly be used to identify curves which differ from that of the majority of the curves studied and therefore are potentially of bad quality.

Therefore, in one aspect, the present invention provides a method of analysis, wherein molecular, particularly biomolecular, interactions at one or more sensing surface areas are detected and respective response curves representing the progress of each interaction with time are produced. According to the invention, a resulting set of response curves is subjected to a quality assessment procedure comprising the steps of:

a) selecting at least one quality-related parameter for the response curves, and for each different parameter defining at least one quality descriptor;

b) computing for each response curve in the set thereof, values for the different quality descriptors;

c) based on the values for the different quality descriptors, computing for each response curve a quality classification indicative of the quality of the response curve in relation to all response curves of the set;

d) selecting response curves having deviating quality classifications; and e) subjecting the selected response curves to a validation procedure to determine whether a response curve or curves are to be rejected or not.

In another aspect, the present invention provides an analytical system for studying molecular interactions, which comprises data processing means for classifying the response curves with regard to quality.

In still another aspect, the present invention provides a computer program comprising program code means for performing the quality assessment procedure.

In a further aspect, the present invention provides a computer system containing a computer program comprising program code means for performing the quality assessment procedure.

In yet another aspect, the present invention provides a computer program product comprising program code means stored on a computer readable medium or carried on an electrical or optical signal for performing the quality assessment procedure.

These and other aspects of this invention will be evident upon review of the attached figures and following detailed description.

DETAILED DESCRIPTION OF THE INVENTION

Figure 1:
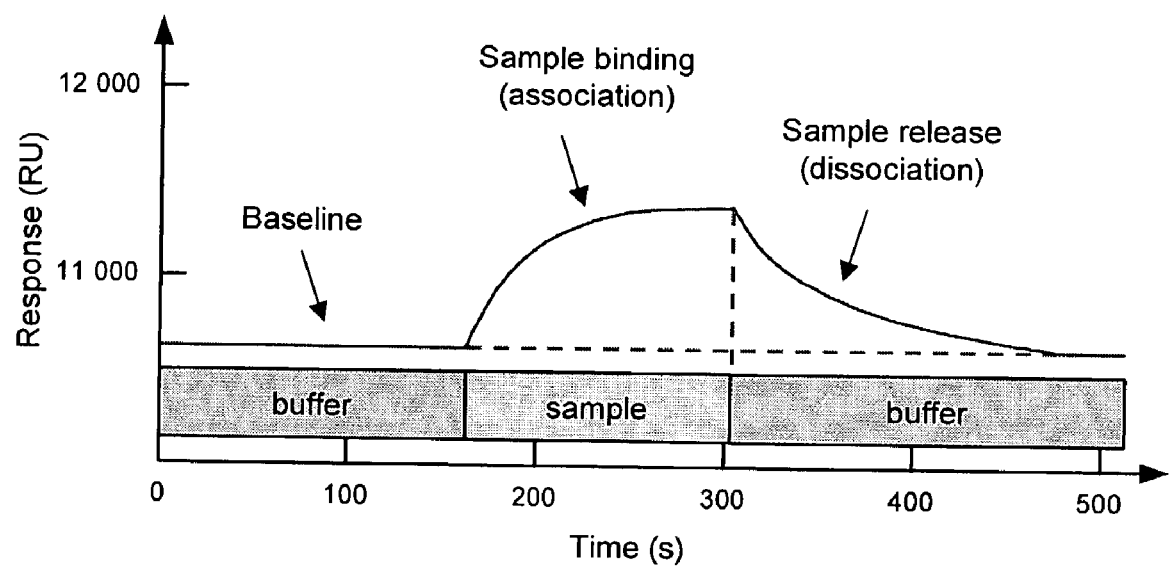
FIG. 1 is a sensorgram showing the interaction between a sample and a target molecule.

As mentioned above, the present invention relates to analytical sensor methods, particularly biosensor based, where molecular interactions are studied and the results are presented in real time, as the interactions progress, in the form of detection curves, often called sensorgrams.

Biosensors may be based on a variety of detection methods. Typically such methods include, but are not limited to, mass detection methods, such as piezoelectric, optical, thermo-optical and surface acoustic wave (SAW) device methods, and electrochemical methods, such as potentiometric, conductometric, amperometric and capacitance methods. With regard to optical detection methods, representative methods include those that detect mass surface concentration, such as reflection-optical methods, including both internal and external reflection methods, angle, wavelength or phase resolved, for example ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging such as critical angle resolved imaging, Brewster angle resolved imaging, SPR angle resolved imaging, and the like. Further, photometric methods based on, for example, evanescent fluorescence (TIRF) and phosphorescence may also be employed, as well as waveguide interferometers.

The presently most commonly used detection principle is surface plasmon resonance (SPR) spectroscopy. An exemplary type of SPR-based biosensors is sold by Biacore AB (Uppsala, Sweden) under the trade name BIACORE® (hereinafter referred to as "the BIACORE instrument"). These biosensors utilize a SPR based mass-sensing technique to provide a "real-time" binding interaction analysis between a surface bound ligand and an analyte of interest.

The BIACORE instrument includes a light emitting diode (LED), a sensor chip including a glass plate covered with a thin gold film, an integrated fluid cartridge providing a liquid flow over the sensor chip, and a photo detector array. Incoming light from the LED is totally internally reflected at the glass/gold interface and detected by the photo detector array. At a certain angle of incidence ("the SPR angle"), a surface plasmon wave is set up in the gold layer which is detected as an intensity loss "or dip" in the reflected light. More particularly, and as is appreciated by those skilled in the art, the phenomenon of SPR associated with the BIACORE instrument is dependent on the resonant coupling of monochromatic p-polarized light, incident on a thin metal film via a prism and a glass plate, to oscillations of the conducting electrons, called plasmons, at the metal film on the other side of the glass plate. These oscillations give rise to an evanescent field which extends a distance of the order of one wavelength ($\approx 1$ μm) from the surface into the liquid flow. When resonance occurs, light energy is lost to the metal film through a collective excitation of electrons therein and the reflected light intensity drops at a sharply defined angle of incidence, the SPR angle, which is dependent on the refractive index within reach of the evanescent field in the proximity of the metal surface.

As noted above, the SPR angle depends on the refractive index of the medium close to the gold layer. In the BIACORE instrument, dextran is typically coupled to the gold surface, with the analyte-binding ligand being bound to the surface of the dextran layer. The analyte of interest is injected in solution form onto the sensor surface through the fluid cartridge. Because the refractive index in the proximity of the gold film depends on (i) the refractive index of the solution (which is constant), and (ii) the amount of material bound to the surface, the binding interaction between the bound ligand and analyte can be monitored as a function of the change in SPR angle.

A detailed discussion of the technical aspects of the BIACORE instrument and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE instrument may be found in U.S. Pat. No. 5,492,840. The full disclosures of the above-mentioned U.S. patents are incorporated by reference herein.

A typical output from the BIACORE instrument is a "sensorgram", which is a plot of response (measured in "resonance units" or "RU") as a function of time. An increase of 1,000 RU corresponds to an increase of mass on the sensor surface of about 1 ng/mm$^2$. As sample containing an analyte contacts the sensor surface, the ligand bound to the sensor surface interacts with the analyte in a step referred to as "association." This step is indicated on the sensorgram by an increase in RU as the sample is initially brought into contact with the sensor surface. Conversely, "dissociation" normally occurs when sample flow is replaced by, for example, a buffer flow. This step is indicted on the sensorgram by a drop in RU over time as analyte dissociates from the surface-bound ligand.

A representative sensorgram for the BIACORE instrument is presented in FIG. 1, which depicts a sensing surface having an immobilized ligand (e.g., an antibody) interacting with analyte in a sample. The y-axis indicates the response (here in resonance units (RU)) and the x-axis indicates the time (here in seconds). Initially, buffer is passed over the sensing surface giving the "baseline response" in the sensorgram. During sample injection, an increase in signal is observed due to binding of the analyte (i.e., association) to a steady state condition where the resonance signal plateaus. At the end of sample injection, the sample is replaced with a continuous flow of buffer and a decrease in signal reflects the dissociation, or release, of analyte from the surface. The slope of the association/dissociation curves provides valuable information regarding the interaction kinetics, and the height of the resonance signal represents surface concentration (i.e., the response resulting from an interaction is related to the change in mass concentration on the surface).

The detection curves, or sensorgrams, produced by biosensor systems based on other detection principles will have a similar appearance.

Figure 2:
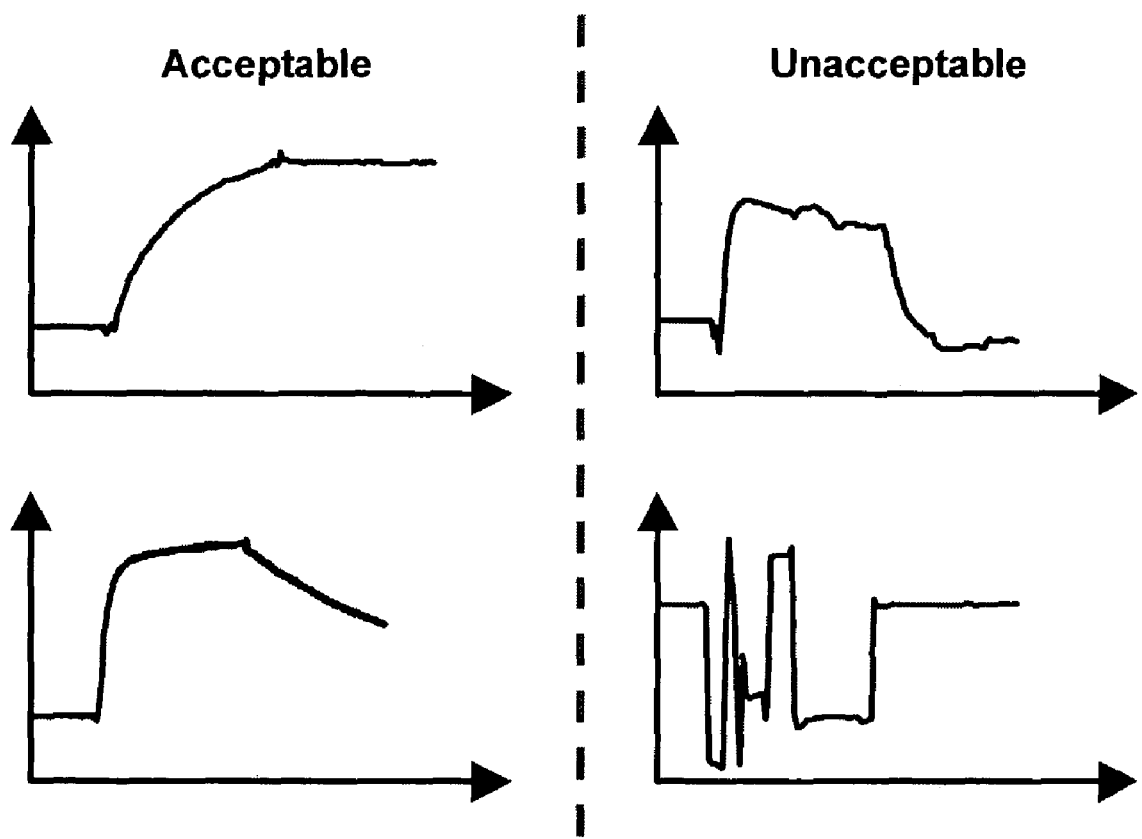
FIG. 2 shows two acceptable (left) and two unacceptable (right) sensorgrams.

Sometimes the sensorgrams produced may for various reasons be of unacceptable quality and therefore have to be discarded. FIG. 2 shows examples of two acceptable and two unacceptable sensorgrams. The two curves to the left are both acceptable. The top-right curve, on the other hand, is too unstable, and the bottom-right curve is deformed due to air-peaks (air bubbles in the fluid flow). Today, a control of the quality of sensorgrams is normally done by the user making an overlay plot of the curves to be analyzed and visually searching for oddities in the curves.

The current trend in biosensor systems is, however, a development towards high throughput systems capable of producing large sets of sensorgrams in a relatively short time. It is readily seen that already with a moderate increase in throughput, it will be impracticable for the user to inspect all the sensorgrams one at a time for assessing the quality thereof.

According to the present invention this problem is overcome by providing for data processing of the sensorgrams to at least substantially assist the user in assessing their quality. An algorithm has been devised, which is applicable in situations where a large set of sensorgrams is studied and classified with regard to quality, for example to identify curves with an odd quality, i.e., which differs from the quality of most of the sensorgrams in the set. The quality of a sensorgram being odd does, however, not necessarily mean that the quality is bad, and the "odd" sensorgrams are therefore subjected to a validation procedure where it is decided if the sensorgram is to be accepted or discarded. The validation procedure includes the use of at least one decision support. One such decision support is ocular (visual) inspection of the sensorgrams. Another decision support includes information on the reason why a sensorgram has been classified as odd. Still another decision support includes information on "time clusters" of odd sensorgrams, i.e., many sensorgrams associated with a specific time period or periods when the sensorgrams were produced. Using one or more of these decision supports, the operator (user) manually removes unaccepted sensorgrams. The validation procedure may also comprise an automated decision support in the form of a "decision algorithm" replacing any manual operation. The procedure of data processing of remaining sensorgrams and inspection of identified odd sensorgrams by the user is then repeated in an iterative manner until no more unacceptable sensorgrams are identified.

Figure 3:
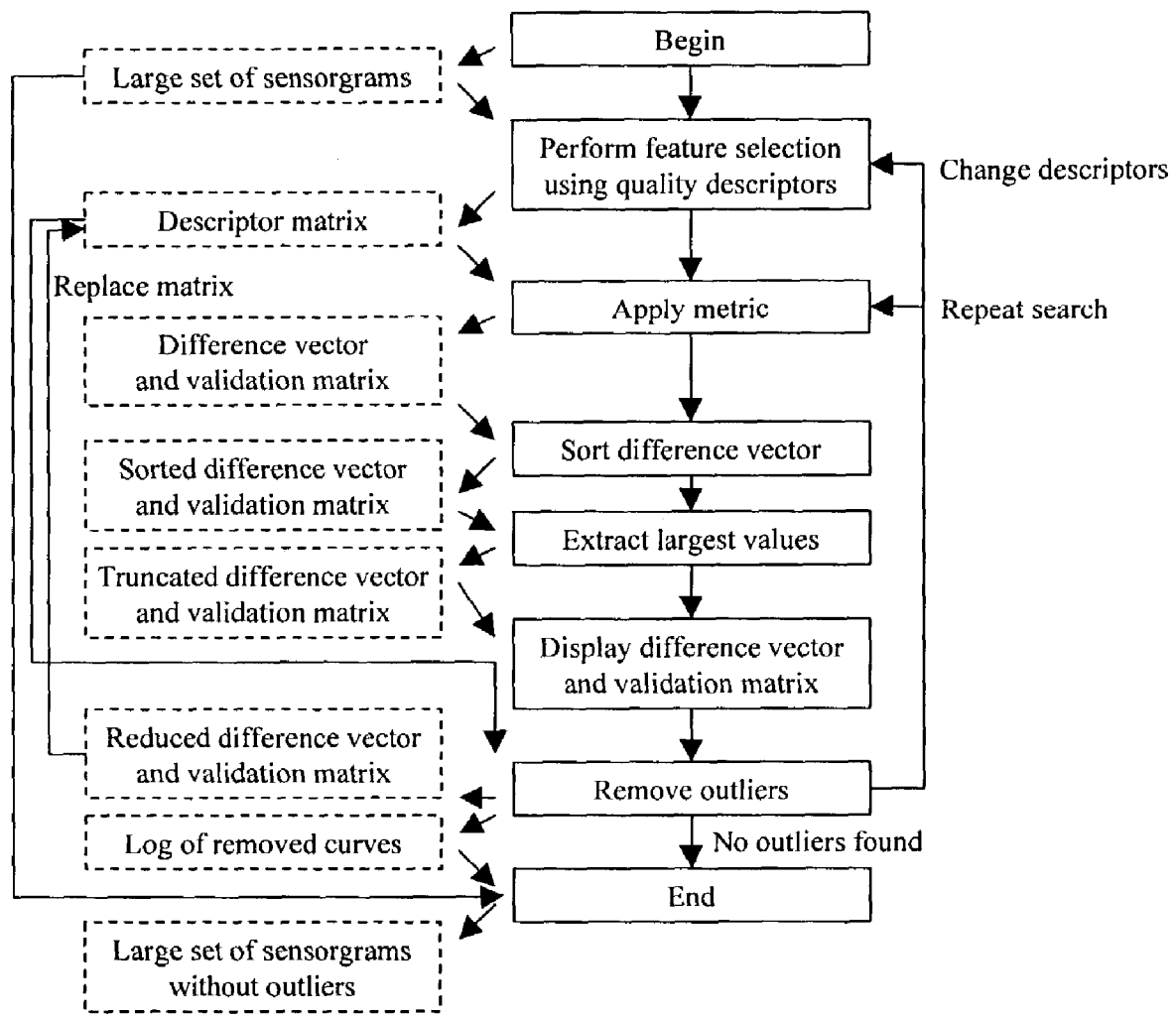
FIG. 3 is a flow chart showing the steps in an exemplary embodiment of the present invention.

A flow chart of an embodiment of the algorithm is shown in FIG. 3. This algorithm is designed to remove curves with a quality different from most of a large set of sensorgrams, so-called "outliers", and basically comprises the steps of (i) representing the sensorgrams with a number of quality descriptors, (ii) applying a quality classification method to the descriptors to find outliers, and (iii) removing the outliers. Preferably, a semi-supervised iterative approach is used.

The process is started with a large set of sensorgrams, usually more than about 100, for example in the range of from about 1000 to 40,000, obtained by running a number of test cycles on a biosensor system, such as, e.g., the BIACORE instrument.

The first step is to select the sensorgram features (curve parameters) used to determine the quality of the sensorgrams. Examples of such features are baseline slope, air spikes, and carry-over between measurements, just to mention a few. While it may be possible to use only a small number of features, such as e.g., three to five different features, it is usually preferred to use at least ten or fifteen different features. Each selected feature of a sensorgram is given a value, herein referred to as a "quality descriptor", which, for example, may be a numerical value or a vector.

The descriptors of each sensorgram are then transformed to a vector of descriptor values. In this way each sensorgram has been reduced to a set of descriptor values representing the different quality parameters. Thus, instead of the sensorgram, there are now a small number of figures in a vector which describe only the properties of interest of the sensorgram. The descriptor vectors for all the sensorgrams in the set are collected in a descriptor matrix.

A quality metric, usually an equation, is then applied to the descriptor matrix to estimate the difference in quality between each sensorgram and the rest of the sensorgrams in the set. This translates the descriptor matrix to a difference vector (containing differences) and validation matrix (containing estimates of the contribution to the difference of each descriptor).

The difference vector is then sorted with regard to difference magnitude to obtain a sorted difference vector and validation matrix.

A predetermined number of the largest difference values are extracted, e.g., the 50 or 100 largest values, to obtain a truncated difference vector and validation matrix, which is displayed to the user. It is understood that sensorgrams with large differences may be outliers with respect to the quality descriptors.

Usually, the user inspects the corresponding sensorgrams (or only a fraction thereof as desired), to decide which sensorgrams have insufficient quality, and removes them (manually) as outliers. As mentioned above and to be described in more detail below, the user may also utilize other types of decision supports. The removed outliers are collected in a log of removed curves, and the remaining sensorgrams (i.e., all sensorgrams minus removed outliers) are represented in a new descriptor matrix (replacing the original descriptor matrix). The search for outliers is repeated by again applying the quality metric equation and proceeding as described above to display the, e.g., 50 new sensorgrams that represent the largest differences. The reason for applying the quality metric equation again is that the metric may use the entire set of sensorgrams as a reference, and the set has changed. The process is repeated until the user cannot find any unacceptable, or bad, sensorgrams among those presented to him, the end result being a large set of sensorgrams without outliers.

As indicated in the flow chart, it is possible to change descriptors when repeating the search.

A basic characteristic of the present invention is the selection of curve quality features and their descriptors. Generally applicable quality features, or parameters, are odd curve shapes, such as baseline slope, spikes (e.g., an air spike during sample injection), oscillations and jumps. Other exemplary quality parameters include carry-over between measurements, binding to a reference surface area, and dissociation to a negative value (below zero). Suitable quality parameters for each particular situation may readily be selected by the skilled person.

Each quality parameter corresponds to one or more descriptors, a descriptor being a formula or algorithm that with one or more sensorgrams as input produces, for example, a numerical value as output. If, for instance, one of the descriptors is oscillations of the baseline, a sensorgram for which the baseline descriptor has the value 10 has a more oscillating baseline than a sensorgram where the descriptor has the value 5. A descriptor measuring the carry-over between measurements in the sensorgram is in its simplest form only a relative response (the response at the end of a buffer injection relative to the baseline level). An example of a descriptor table (matrix) is given in Table 1 below.

TABLE 1

| Cycle | Baseline slope | Carry-over | Air spike |
| --- | --- | --- | --- |
| 1 | 2.0 | 4.5 | 0.185 |
| 2 | 0.1 | 4.8 | 0.036 |
| 3 | 2.0 | 4.5 | 0.272 |
| 4 | 1.1 | 4.8 | 0.082 |
| 5 | 2.3 | 4.4 | 0.036 |

Another type of descriptor will be described with reference to FIGS. 4 and 5. While FIG. 2 referred to above shows some examples of unacceptable sensorgrams, additional examples are given in FIG. 4 which shows an overlay plot of five acceptable (good) and four unacceptable (bad) sensorgrams. As to the latter, A and B are affected by disturbances during dissociation, C has a discontinuity in the association phase, and D has a dissociation level less than zero.

Figure 4:
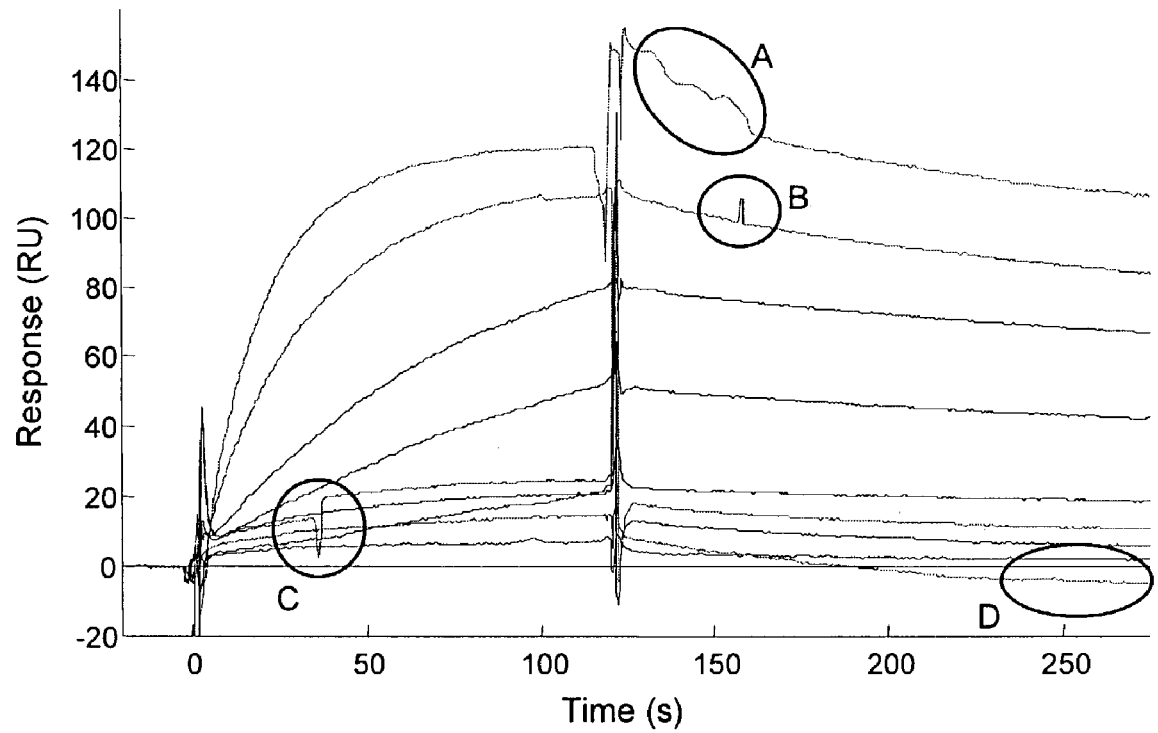
FIG. 4 is an overlay plot of five good and four bad sensorgrams with disturbances indicated at A, B, C and D.
Figure 5:
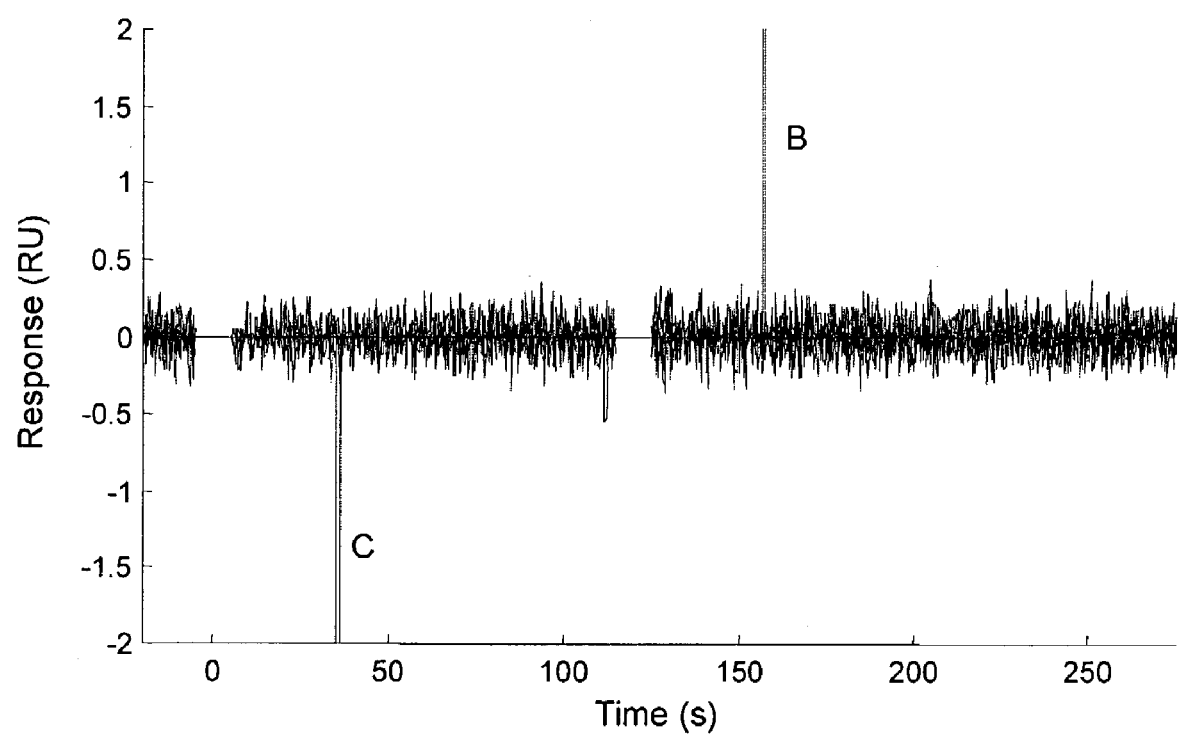
FIG. 5 is an illustration of a sensorgram where long term changes have been eliminated by a filter, whereas short term fluctuations at B and C are retained.

FIG. 5 illustrates the sensorgrams in FIG. 4 after applying to each sensorgram a filter that eliminates longer term fluctuations while retaining short-term fluctuations. As seen in FIG. 5, the maximum deviation from zero for the resulting curves are clearly largest for B and C. Utilizing this value as a primitive descriptor, B and C can be detected as different from the rest of the set.

Another basic characteristic of the present invention is the classification of the sensorgrams with regard to their quality by applying a quality classification method. Each sensorgram is represented by a descriptor vector, and the descriptor vectors are collected in a descriptor matrix. To classify the sensorgrams by quality, it is determined how similar the sensorgrams are to each other. The quality classification method may, for example, comprise the use of a quality metric, usually an equation, as described with regard to FIG. 3 above. Alternative classification methods include the use of a cluster algorithm, e.g., a KNN cluster algorithm, which classifies the sensorgrams in groups having a similar quality; a neural network or an expert system. All these quality classification methods are per se well-known to a person skilled in the art.

When, for example, a quality metric equation is used, each vector may be seen as a point in space, and the similarity between sensorgrams may then be represented by the distances between the respective points.

To measure the distances between the descriptor vectors, a statistical method may be used which measures the distance from each respective vector to all the other vectors seen as a group. Thereby each vector is reduced to a single value that describes how similar the descriptor vector is to all the other vectors. Sensorgrams having approximately the same value are then about equal qualitywise regarding the descriptors and the statistical method. Statistical methods that may be used include methods that are per se well known to the skilled person. Some specific exemplary methods are briefly described below.

"Mahalanobis distance" is a generalisation of the Euclidian distance between two points. Areas with a constant distance are ellipsoids centered around the mean value. When the descriptors are uncorrelated and the variances are equal to one in all directions, the areas are spheres and the Mahalanobis distance is equivalent to the Euclidian distance. The measure as such comprises a normalization of the descriptors by means of the inverse of the covariance matrix.

"Manhattan distance" sums up the descriptor vector.

"Principal component 1 vs 2" returns the score vectors 1 and 2 for the descriptor matrix. In contrast to the other methods mentioned above, this method does not provide any ranking.

The quality classification may include resealing, or "normalizing", the descriptor values to make them comparable. An exemplary normalization method is the "mean centre" method, which sets the mean value of the descriptor values to zero. Other examples of normalization procedures are "mean centre and unit variance" (sets the mean value of the descriptors to zero and variance to one), and "unit variance" (sets variances to one).

As mentioned above, it is possible to change descriptors between reiterations of the outlier detection procedure (see FIG. 3). It is to be noted, however, that also the normalization and/or the quality classification method may be changed before each reiteration.

As also mentioned above, the user makes use of at least one "decision support" when validating the sensorgrams classified as odd. Thus, usually, the user obtains a visual plot of the classification result, and based thereon displays sensorgrams to be validated for possible removal. The user may, however, alternatively, or additionally, obtain information on which specific descriptor or descriptors that caused a particular classification of a sensorgram. He may also alternatively, or additionally, obtain information on time periods during the production of the sensorgrams to which many odd sensorgrams in a set may be related ("time clusters"). Alternatively, however, the whole validation procedure may be carried out by a decision algorithm without assistance by the user.

The above described quality assessment procedure is readily reduced to practice in the form of a computer system running software which implements the steps of the procedure. The invention also extends to computer programs, particularly computer programs on or in a carrier, adapted for putting the quality assessment procedure of the invention into practice. The carrier may be any entity or device capable of carrying the program. For example, the carrier may comprise a storage medium, such as a ROM, a CD ROM or a semiconductor ROM, or a magnetic recording medium, for example a floppy disc or a hard disk. The carrier may also be a transmissible carrier, such as an electrical or optical signal which may be conveyed via electrical or optical cable or by radio or other means. Alternatively, the carrier may be an integrated circuit in which the program is embedded.

While any suitable computer language may be used to implement the present invention, it is currently preferred to use a suite of MATLAB™ module files (The MathWorks, Inc., Natick, Mass., U.S.A.).

The invention will be further illustrated by the following non-limiting Example.

EXAMPLE

Eleven sensorgrams (below referred to as RU 1 to 11) were extracted from test data obtained with a BIACORE® 3000 (Biacore AB, Uppsala, Sweden). These sensorgrams were used to successfully run a simple embodiment of the algorithm outlined in FIG. 3 in MATLAB 5.3.1.29215a (R11.1) (The MathWorks, Inc., Natick, Mass., U.S.A.), using a PC with Windows NT 4.0. As descriptors were used (i) negative dissociation ("negd2"), (ii) jumpy association region ("assjmpmedian"), and (iii) jumpy dissociation region ("dissjmpmedian"). The metric used was the norm of the difference between the descriptors and the mean of the descriptor matrix. The program and the sensorgrams (values) are shown below.

```
%program begin
function example
%load sensorgrams
[t,RU]=getRU;
%get descriptor values:
negd2=desc_negd2(t,RU,200); %define d2 at time 200s
assjmpmedian=desc_jmpmedian(t,RU,10,100); %define association region to 10-100 s
dissjmpmedian=desc_jmpmedian(t,RU,130,180); %define dissociation region to 130-
180 s
%make descriptor matrix
descr_matrix=[negd2(:) assjmpmedian(:) dissjmpmedian(:)];
%prepare for plot
figh=figure;clf,hold on
for j=1:size(RU,1)
    lhblue(j)=plot(t,RU(j,:),'b');
end
```

```
%in the first round, include all sensorgrams
include=logical(ones(size(RU,1),1));
%perform 5 iterations (this should be user defined)
for j=1:5
    %mean of descriptor values for included sensorgrams
    descr_matrix_mean=mean(descr_matrix(include,:));
    for k=1:size(RU,1)
        %apply a simple metric: the norm of the difference between
        %the descriptors for a sensorgram and the mean of the descriptor matrix
        if include(k)
            descrdist(k)=norm(descr_matrix(k,:)-descr_matrix_mean);
        else
            %sensorgram already excluded
            descrdist(k)=0;
        end
    end
    %identify most deviating sensorgram
    [tmp,max_index]=max(descrdist);
    %plot most deviating sensorgram in red
    lh=plot(t,RU(max_index,:),'r');
    title('worst curve in red')
    pause(3)
    %remove most deviating sensorgram from future calculations and from the plot
    include(max_index)logical(0);
    delete(lh)
    delete(lhblue(max_index));
    title('removing worst curve and recalculate metric')
    pause(1)
end
cla
title('Exiting demo...')
pause(1)
delete(figh)
%%%%%%%%%%%% Local functions %%%%%%%%%%%%%%%%%%%%
function negd2=desc_negd2(t,RU,d2)
% negd2=desc_negd2(t,RU,d2) Descriptor for negative dissociation values
%t    : time vector
%RU : Sensorgram matrix, one sensorgram per row.
%d2 : time defining the d2 reportpoint
[tmp,d2_index]=min(abs(t-d2));
if d2_index==length(t)
    d2_index=length(t)-1;
end
for j=1:size(RU,1)
    negd2(j)=mean(RU(j,d2_index-1:d2_index+1));
    if negd2(j)>0
        negd2(j)=negd2(j)/1000;
    else
        negd2(j)=-negd2(j);
    end
end
function jmpmedian=desc_jmpmedian(t,RU,start,stop)
% jmpmedian=desc_jmpmedian(t,RU,start,stop) Descriptor for jumpy sensorgrams
%t    : time vector
%RU   : Sensorgram matrix, one sensorgram per row.
%start : time defining start of interval where jumps should be identified
%stop : time defining stop of interval where jumps should be identified
[tmp,start_index]=min(abs(t-start));
[tmp,stop_index]=min(abs(t-stop));
for j=1:size(RU,1) %for all sensorgrams
    l=1;
    for k=start_index+1:stop_index-1
        tmp(1)=RU(j,k)-median(RU(j,k-1:k+1));
        l=l+1;
    end
    tmp=sort(abs(tmp));
    jmpmedian(j)=sum(tmp(end-2:end))/3;
end
function [t,RU]=getRU
% Sensorgrams used in this example
t=[  -20  -18  -16  -14  -12  -10   -8   -6   -4   -2  ...
       0    2    4    6    8   10   12   14   16   18  ...
      20   22   24   26   28   30   32   34   36   38  ...
      40   42   44   46   48   50   52   54   56   58  ...
      60   62   64   66   68   70   72   74   76   78  ...
      80   82   84   86   88   90   92   94   96   98  ...
     100  102  104  106  108  110  112  114  116  118  ...
```

-continued

```
        120    122    124    126    128    130    132    134    136    138    ...
        140    142    144    146    148    150    152    154    156    158    ...
        160    162    164    166    168    170    172    174    176    178    ...
        180    182    184    186    188    190    192    194    196    198    ...
        200    202    204    206    208    210    212    214    216    218    220]';
RU(1,:)=[   -0.08   0.00  -0.13  -0.11   0.00  -0.15  -0.14  -0.01  -0.09  -2.73   1.78  -27.55  ...
            -7.29   1.57   2.89   3.73   4.20   3.95   4.54   4.73   5.18   5.08   5.48   5.59   5.82  ...
             6.02   6.27   6.42   6.34   6.58   6.77   6.71   6.70   6.52   6.92   6.84   6.75   7.10  ...
             7.19   7.33   7.24   7.27   7.33   7.51   7.50   7.66   7.67   7.55   7.88   7.72   7.77  ...
             8.00   8.18   8.45   8.26   8.25   8.25   8.25   8.37   8.40   8.63   8.61   8.74   8.39  ...
             8.42   8.71   8.71   8.63   8.68   8.84  10.17  20.90  11.63   7.14   6.20   5.94   5.39  ...
             5.09   5.02   4.92   4.59   4.66   4.71   4.37   4.26   4.27   4.22   4.14   4.08   4.06  ...
             3.92   3.87   3.72   3.62   3.66   3.73   3.65   3.60   3.46   3.52   3.45   3.48   3.37  ...
             3.34   3.14   3.05   3.22   3.06   3.09   2.93   3.03   2.90   2.73   3.02   2.96   2.93  ...
             2.68   2.69   2.84   2.73   2.64   ];
RU(2,:)=[   -0.06   0.11   0.07   0.19  -0.01   0.20   0.06  -0.08   0.24   0.09  -4.11   1.74   ...
            -5.48   2.55   4.03   4.46   4.98   4.57   4.92   5.42   5.65   6.01   6.40   6.79   6.71  ...
             6.54   6.86   6.85   7.20   6.98   7.28   7.33   7.30   7.45   7.51   7.45   7.69   7.79  ...
             8.14   7.97   8.41   8.30   8.42   8.51   8.72   8.60   8.88   8.87   8.57   8.70   8.67  ...
             9.05   9.31   9.47   9.36   9.39   9.74   9.28   9.05   9.16   9.10   8.99   9.10   9.24  ...
             9.37   9.18   9.44   9.39   9.28   9.49  10.51   7.89  10.48   6.79   6.27   5.79   5.33  ...
             5.19   5.06   5.08   4.94   4.77   4.61   4.74   4.94   4.74   4.73   4.39   4.33   4.56  ...
             4.49   4.36   4.66   4.37   4.68   4.31   4.35   4.16   3.92   4.14   4.15   4.04   4.06  ...
             4.10   3.85   3.91   3.77   3.81   3.81   3.70   3.72   3.94   3.90   3.70   3.95   3.62  ...
             3.35   3.32   3.34   3.32   3.50   ];
RU(3,:)=[    0.06   0.08  -0.01   0.10  -0.03  -0.10  -0.24  -0.09   0.08  -0.88   1.88  -0.93   ...
            19.98   9.72   8.96   9.53  10.17  10.66  11.21  11.52  12.19  12.76  13.37  13.63  14.00  ...
            14.37  14.59  15.03  15.37  15.59  15.73  16.05  16.28  16.45  16.77  16.92  17.39  17.39  ...
            17.69  17.96  17.93  18.12  18.36  18.69  18.94  19.13  19.31  19.59  19.54  19.76  ...
            19.72  20.02  20.13  20.19  20.35  20.29  20.52  20.41  20.64  20.50  20.33  20.81  20.77  ...
            20.75  20.90  20.38  21.04  21.02  20.93  21.77 -10.02   9.85  13.08  13.23  13.01  12.42  ...
            12.51  12.03  11.74  11.64  11.45  11.33  10.99  11.24  10.93  10.84  10.58  10.55  10.30  ...
            10.10   9.88   9.82   9.54   9.49   9.38   9.38   9.28   9.27   9.14   9.03   8.70   8.73  ...
             8.63   8.70   8.55   8.54   8.34   8.43   8.42   8.19   7.97   8.20   8.00   7.80   7.57  ...
             7.72   7.47   7.55   7.18   7.32   ];
RU(4,:)=[   -0.21   0.18   0.14  -0.02  -0.04   0.00   0.09   0.01   0.10  -4.03   1.48  -7.03   ...
             0.66   3.28   3.19   4.02   3.93   3.96   4.16   4.28   4.72   4.86   5.07   5.44   5.22  ...
             5.49   5.40   5.84   5.73   5.86   5.86   5.86   5.95   5.83   5.95   5.97   6.14   6.07  ...
             6.40   6.16   6.25   6.59   6.46   6.43   6.59   6.72   6.39   6.57   6.44   6.39   6.43  ...
             6.55   6.68   6.84   6.64   6.62   6.71   7.21   7.61   8.07   7.38   7.07   6.97   6.83  ...
             7.07   6.86   7.06   7.03   7.10   7.73   8.07   9.14   5.66   4.73   4.13   3.99   3.78  ...
             3.69   3.51   3.33   3.57   3.42   3.60   3.71   3.39   3.35   3.31   3.27   3.02   3.11  ...
             3.45   3.10   3.31   2.91   3.01   2.91   2.71   2.90   3.09   2.71   2.88   2.91   2.66  ...
             2.72   2.68   2.71   2.55   2.56   2.52   2.50   2.59   2.41   2.30   2.35   2.23   2.31  ...
             2.20   2.13   2.55   1.95   2.03   ];
RU(5,:)=[   -0.03  -0.08  -0.21   0.01  -0.14  -0.06  -0.01  -0.17  -0.05  -3.98   1.25   0.35   ...
             4.46   5.54   6.26   6.77   7.12   7.51   7.59   8.09   8.44   8.54   9.12   9.35   9.39  ...
             9.96  10.00  10.05  10.40  10.76  10.71  11.07  10.96  11.23  11.31  11.41  11.46  11.58  ...
            11.83  12.06  12.19  12.39  12.49  12.54  12.64  12.79  12.96  12.98  13.13  12.98  13.61  ...
            13.40  13.41  13.40  13.70  13.84  14.05  13.93  13.90  14.26  14.19  14.07  14.30  14.40  ...
            14.47  14.54  14.76  14.45  14.44  14.75  14.95  14.70   8.99   8.04   7.64   7.44   7.10  ...
             6.74   6.19   5.97   5.82   5.52   5.19   4.86   4.50   4.41   3.85   3.84   3.84   3.50  ...
             3.36   2.85   2.55   2.23   2.09   2.09   1.65   1.37   1.11   0.91   0.77   0.62   0.56  ...
             0.57   0.07   0.21  -0.35  -0.50  -0.72  -1.15  -1.07  -1.33  -1.53  -1.47  -1.81  -2.22  ...
            -2.52  -2.82  -2.92  -3.06  -3.29   ];
RU(6,:)=[   -0.18   0.15   0.19  -0.07   0.03   0.00   0.00   0.00   0.02  -0.11  -0.18   1.83  -0.27   ...
            19.85   9.20   8.63   9.04   9.55  10.23  10.53  11.20  11.54  11.89  12.05  12.50  13.00  ...
            13.18  13.57  13.73   5.42  19.88  20.19  20.41  20.58  20.82  21.28  21.42  21.36  21.68  ...
            21.97  21.98  22.06  22.43  22.36  22.49  22.75  22.88  23.18  23.30  23.77  23.75  23.87  ...
            24.05  24.02  24.21  24.03  24.30  24.17  24.36  24.50  24.53  24.62  24.83  24.51  24.52  ...
            24.60  24.85  24.85  24.68  24.65  24.56  25.68  22.94  11.59  17.61  17.79  17.55  17.37  ...
            17.14  17.03  16.61  16.37  16.38  16.00  15.79  15.83  15.57  15.40  15.27  15.10  15.01  ...
            14.72  14.56  14.50  14.43  14.49  14.35  14.10  13.93  13.89  13.81  13.65  13.60  13.47  ...
            13.48  13.31  13.25  13.29  13.21  13.03  12.98  13.00  12.92  12.77  12.62  12.57  12.66  ...
            12.56  12.56  12.46  12.40  12.07   ];
RU(7,:)=[    0.03   0.17   0.15   0.05   0.15   0.04   0.11   0.00   0.21  -0.06  -4.46   1.71   ...
            -1.57  19.16  30.89  40.91  49.48  56.82  63.32  69.11  74.23  78.98  83.22  86.66  89.90  ...
            92.68  95.39  97.63 100.02 101.82 103.31 104.68 106.24 107.34 108.43  ...
           109.52 110.48 111.52 112.21 112.96 113.69 114.46 114.94 115.50  ...
           115.83 116.32 116.35 116.91 117.28 117.77 118.05 118.37 118.99  ...
           119.37 119.48 119.24 119.43 119.35 119.55 119.48 119.81 120.04  ...
           120.15 120.06 120.40 120.49 120.50 120.54 110.69  97.19 149.78  ...
           147.83 154.35 148.98 148.45 148.33 147.61 145.04 141.08 139.11  ...
           138.51 138.55 138.36 137.15 135.17 134.42 135.22 134.41 132.57  ...
           129.90 124.93 123.63 122.95 122.48 122.07 121.61 120.86 120.59  ...
           120.22 119.60 119.36 118.87 118.48 118.20 117.72 117.32 116.97  ...
           116.61 115.96 115.89 115.71 115.20 114.90 114.57 114.47 114.01  ...
           113.78 113.36 112.91 112.67 112.54   ];
```

-continued

```
RU(8,:)=[    -0.15    0.01    0.14   -0.06   -0.33   -0.11   -0.11   -0.05    0.06   -4.19    2.10   -7.52  ...
              1.46    3.43    4.21    4.22    4.65    5.01    5.29    5.55    5.93    6.10    6.24    6.35    6.75  ...
              7.10    7.43    7.90    7.94    7.98    8.38    8.60    9.23    9.78   10.17   10.81   11.09   11.39  ...
             11.98   12.24   12.54   12.85   12.99   13.60   13.80   14.14   14.55   14.88   15.13   15.55   16.11  ...
             16.57   16.88   16.86   17.00   17.43   17.52   17.36   17.71   17.91   18.41   18.40   18.95   19.50  ...
             19.94   20.18   20.79   20.87   21.14   21.62   23.35   34.38   24.68   22.95   22.75   22.50   22.30  ...
             22.23   22.00   22.14   22.01   21.73   21.84   21.42   21.49   21.63   21.60   21.46   21.42   21.40  ...
             21.25   21.25   21.41   21.31   21.23   21.21   20.85   20.79   20.82   20.85   20.73   20.83   20.57  ...
             20.32   20.43   20.41   20.58   20.44   20.44   20.33   20.16   20.23   20.20   20.32   20.24   20.17  ...
             20.17   19.94   19.89   19.68   19.69   ];
RU(9,:)=[    -0.10    0.02    0.20    0.28    0.15    0.25    0.21    0.01    0.03    0.26   -3.95    3.38  ...
              9.31    9.22   10.93   12.99   15.43   17.57   20.22   21.79   23.74   25.67   27.47   29.03   30.89  ...
             32.67   34.19   36.07   37.68   39.25   40.91   42.60   44.30   45.88   47.20   48.75   50.11   51.39  ...
             52.63   53.78   54.97   56.26   57.28   58.69   59.71   61.02   61.77   62.71   63.80   64.97   65.74  ...
             66.63   67.21   67.94   68.81   69.40   70.21   71.25   71.99   72.80   73.35   74.05   74.96   75.74  ...
             76.48   77.06   77.72   78.46   78.84   79.56   81.21   77.98   79.72   79.44   79.45   79.28   78.97  ...
             78.66   78.14   77.82   77.53   77.23   76.94   76.89   76.65   76.55   76.04   76.02   75.87   75.62  ...
             75.40   75.33   74.77   74.87   74.81   74.46   74.27   74.06   73.87   73.88   73.44   73.46   73.26  ...
             73.12   72.84   72.80   72.38   72.35   72.22   72.26   71.96   71.70   71.62   71.49   71.31   70.94  ...
             70.82   70.73   70.56   70.11   70.19   ];
RU(10,:)=[    0.06    0.05    0.29    0.21    0.14    0.05   -0.05   -0.02   -0.08   -4.39    1.27  -10.02  ...
              4.29   15.49   22.44   28.56   34.04   38.49   42.82   47.43   51.14   55.06   58.25   61.46   64.65  ...
             67.19   69.92   72.15   74.49   76.78   78.42   80.43   82.20   83.79   85.73   87.16   88.63   89.85  ...
             91.22   92.20   93.22   94.30   95.14   96.01   96.98   98.13   98.91   99.65  100.28  100.88   ...
            101.36  102.19  103.02  103.37  103.77  104.17  104.60  104.98  105.53   ...
            105.87  106.12  105.15  105.24  105.43  105.70  105.66  106.07  106.16   ...
            106.33  107.40  108.21  110.54  107.78  106.26  105.59  105.03  104.48   ...
            103.88  103.21  102.71  102.03  101.59  101.32  101.01  100.73  100.22   ...
             99.65   99.10   98.75  100.51   97.67   97.46   97.15   96.73   96.45   96.02   95.59   95.50   95.28  ...
             94.79   94.80   94.31   94.14   93.63   93.34   93.12   92.86   92.53   92.22   92.21   91.63   91.51  ...
             91.27   91.07   90.97   90.54   90.49   90.25   89.91   89.86   89.34   ];
RU(11,:)=[   -0.02   -0.03    0.05    0.20    0.18    0.14   -0.03    0.16    0.18   -1.75    1.86    4.45  ...
             10.01    7.47    8.13    9.06   10.36   11.77   13.12   13.57   14.93   15.91   16.70   17.66   18.66  ...
             19.53   20.42   21.40   22.13   23.41   24.34   25.08   26.15   27.21   28.00   28.79   29.74   30.71  ...
             31.66   32.00   33.08   34.09   34.91   35.65   36.53   37.56   38.20   38.92   39.52   40.06   40.97  ...
             41.40   42.17   42.63   43.46   44.14   44.65   45.28   45.78   46.19   47.23   47.87   48.35   49.07  ...
             49.77   50.04   50.53   51.05   51.69   52.31   54.11   60.77   50.17   51.08   51.18   50.80   50.53  ...
             50.27   50.12   50.01   49.76   49.58   49.54   49.44   49.22   48.78   48.80   48.84   48.71   48.67  ...
             48.38   48.35   48.27   48.14   47.84   47.88   47.59   47.43   47.15   47.07   46.97   47.04   46.77  ...
             46.82   46.50   46.29   46.13   45.87   46.21   46.01   45.92   45.82   45.65   45.61   45.30   45.42  ...
             45.31   45.02   45.03   44.96   44.88   ];
%program end
```

It is to be understood that the invention is not limited to the particular embodiments of the invention described above, but the scope of the invention will be established by the appended claims.

The invention claimed is:

1. A method of analysis, comprising:
   A) detecting molecular binding interactions between analytes in a sample and molecular structures immobilized on one or more sensing surface areas of a biosensor;
   B) producing a plurality of binding response curves to form a resulting set, each response curve representing a binding interaction of an analyte with a molecular structure over time, each response curve comprising an analyte association part and an analyte dissociation part;
   C) subjecting the resulting set of response curves to a data-processing procedure for assessment of a quality of each of the response curves with respect to a presence of oddities in the response curves, the subjecting operation comprising the substeps of:
      1) selecting at least two quality-related parameters for the response curves, each of the parameters defining a quality descriptor;
      2) computing for each response curve, values for the quality descriptors, which represent the quality of the response curve;
      3) based on the values for the quality descriptors, classifying the response curves by computing for each response curve a quality classification which indicates a deviation of the quality descriptors of the corresponding response curve from the quality descriptors of the other response curves in the resulting set produced in the producing operation;
      4) selecting a predetermined number of the response curves having quality classifications corresponding to the largest deviations, and defining the predetermined number of response curves as odd quality response curves;
      5) displaying the odd quality response curves to a user of the biosensor for visual inspection thereof to thereby decide if an odd quality response curve should be used in the analysis or be rejected;
      6) removing odd quality response curves rejected by the user;
      7) repeating steps 3) to 6) until no more of the odd quality curves are rejected; and
      8) determining from the remaining response curves at least one of molecular surface concentrations and kinetic parameters.

2. The method of claim 1, wherein the substep 2) further comprises transforming the quality descriptor values for each response curve to a quality descriptor vector.

3. The method of claim 2, wherein a quality descriptor matrix is created from the quality descriptor vectors.

4. The method of claim 1, wherein the quality descriptor values are normalized.

5. The method of claim 2, wherein computing a quality classification in the substep 3) further comprises determining for each quality descriptor vector the difference between the quality descriptor vector and the rest of the quality descriptor vectors in the resulting set of response curves.

6. The method of claim 5, wherein the determination of the differences between the quality descriptor vectors comprises determining a statistical measure of the distance from each quality descriptor vector to the rest of the quality descriptor vectors as a group.

7. The method of claim 5, wherein a difference vector is created from the computed differences.

8. The method of claim 5, wherein the substep 4) further comprises sorting the quality descriptor vectors for the resulting set of response curves in order of computed difference, and selecting as odd response curves a predetermined fraction of the response curves corresponding to those having the largest differences.

9. The method of claim 1, wherein computing a quality classification in the substep 3) further comprises classifying the resulting set of response curves in groups of similar quality descriptor values.

10. The method of claim 1, wherein the quality classification is obtained by a neural network.

11. The method of claim 1, wherein the quality classification is obtained by an expert system.

12. The method of claim 1, wherein substep 5) further comprises determining which quality descriptor or descriptors caused the quality classification of a response curve.

13. The method of claim 1, wherein substep 5) further comprises identifying a time period or periods in the production of the response curves to which a cluster of selected response curves may be related.

14. The method of claim 1, wherein the quality parameters on which the quality descriptors are based comprise at least one of an odd curve shape, carry-over between measurements, binding to a reference surface, and dissociation to a value below zero.

15. The method of claim 14, wherein the odd curve shape is selected from sloping baseline, spikes, oscillations and jumps.

16. The method of claim 1, wherein the substeps 3) to 6) are replaced with a different quality classification method.

17. The method of claim 1, wherein the biosensor is based on evanescent wave sensing.

18. A computer-implemented method of analysis, comprising:
    A) detecting molecular binding interactions between analytes in a sample and molecular structures immobilized on one or more sensing surface areas of a biosensor;
    B) producing a plurality of binding response curves to form a resulting set, each response curve representing a binding interaction of an analyte with a molecular structure interaction over time, each response curve comprising an analyte association part and an analyte dissociation part;
    C) subjecting the resulting set of response curves to a data-processing procedure for assessment of a quality of each of the response curves with respect to a presence of oddities in the response curves comprising the subjecting operation comprising the substeps of:
        1) selecting at least two quality-related parameters for the response curves, each of the parameters defining a quality descriptor;
        2) computing for each response curve, values for the quality descriptors, which represent the quality of the response curve;
        3) based on the values for the quality descriptors, classifying the response curves by computing for each response curve a quality classification which indicates a deviation of the quality descriptors of the corresponding response curve from the quality descriptors of the other response curves in the resulting set produced in the producing operation;
        4) selecting a predetermined number of the response curves having quality classifications corresponding to the largest deviations, and defining the predetermined number of response curves as odd quality response curves;
        5) displaying the at least odd quality response curves to a user of the biosensor for visual inspection thereof to thereby decide if an odd quality response curve should be used in the analysis or be rejected;
        6) removing odd quality response curves rejected by the user;
        7) repeating steps 3) to 6) until no more of the odd quality curves are rejected; and
        8) determining from the remaining response curves at least one of molecular surface concentrations and kinetic parameters.

19. The method of claim 1, wherein the biosensor is based on surface plasmon resonance.

* * * * *